United States Patent [19]

Arora et al.

[11] Patent Number: 5,367,062
[45] Date of Patent: Nov. 22, 1994

[54] DISUBSTITUTED AND DEOXYDISUBSTITUTED DERIVATIVES OF ALPHA-D-LYXOFURANOSIDES HAVING ANTI-INFLAMMATORY AND ANTI-PROLIFERATIVE ACTIVITY

[75] Inventors: Sudershan K. Arora, Lansdale; Peter J. Schied, Southampton, both of Pa.

[73] Assignee: Medicarb Inc., Southampton, Pa.

[21] Appl. No.: 933,312

[22] Filed: Aug. 21, 1992

[51] Int. Cl.$^5$ ............... C07H 15/04; C07H 17/02
[52] U.S. Cl. .................... 514/25; 536/17.2; 536/17.5; 536/4.1; 536/1.11; 536/18.7; 536/28.6; 536/18.6; 536/18.5; 536/54; 536/55; 536/29.1; 536/22.1; 536/17.3; 536/28.1; 536/29.11; 514/23; 514/32; 514/24
[58] Field of Search ........... 536/17.2, 17.5, 4.1, 536/1.11, 18.7, 28.6, 18.6, 54, 55, 17.3; 514/23, 25

[56] References Cited

U.S. PATENT DOCUMENTS

| | | | |
|---|---|---|---|
| 2,875,194 | 2/1959 | Baker et al. | 536/17.3 |
| 3,767,800 | 10/1973 | Buzzolini | 514/25 |
| 4,017,608 | 4/1977 | Gordon | 514/25 |
| 4,192,868 | 3/1980 | Tronchet et al. | 514/23 |
| 4,251,520 | 2/1981 | Bruzzese et al. | 536/4.1 |
| 4,996,195 | 2/1991 | Ronsen et al. | 514/23 |
| 5,010,058 | 4/1991 | Ronsen et al. | 514/23 |

OTHER PUBLICATIONS

Barbat et al, "Reactions of D–lyxose and D–xylose with 2 methoxypropene," Carb. Res. 219: 115–121 (1991).
Schmidt, "Isopropylidene Derivates," in "Methods in Carbohydrate Chemistry," Whistler et al. (Eds.), (1963), pp. 318–325.
Pigman, "Chemistry of Carbohydrates," pp. 189–193, 228–231 (1948).
Morrison & Boyd, "Organic Chemistry" (4th Ed.), pp. 523–524 (1983).
The Merck Index, Windholz et al (Eds.), (1983), pp. 1231.

Primary Examiner—Douglas W. Robinson
Assistant Examiner—F. C. Prats
Attorney, Agent, or Firm—Oblon, Spivak, McClelland, Maier & Neustadt

[57] ABSTRACT

Derivatives of disubstituted and deoxydisubstituted α-D-lyxofuranosides and intermediates for preparing these derivatives are described. These compounds exhibit significant antiinflammatory and anti-proliferative activity and are useful for treating inflammatory and/or autoimmune disorders such as psoriasis, asthma, atopic dermatitis, rheumatoid arthritis, osteoarthritis, scleroderma, systemic lupus erythematosus, and cancer (particularly melanoma and colon cancer).

12 Claims, No Drawings

DISUBSTITUTED AND DEOXYDISUBSTITUTED DERIVATIVES OF ALPHA-D-LYXOFURANOSIDES HAVING ANTI-INFLAMMATORY AND ANTI-PROLIFERATIVE ACTIVITY

BACKGROUND OF THE INVENTION

1. Field of the Invention

The present invention relates to novel disubstituted or deoxydisubstituted α-D-lyxofuranosides, their synthesis, and intermediates for preparing these compounds. More specifically, the present invention relates to alkyl, alkoxyalkyl, or aralkyl 2,3-0-(1-methlethylidene)-α-D-lyxofuranosides unsubstituted or substituted at the 5-position. This invention further relates to the replacement of oxygen at 5-position of lyxofuranosides by N or S to form 5-deoxy-5-amino substituted or 5-deoxy-5-thio substituted lyxofuranosides. These compounds show significant anti-inflammatory and anti-proliferative activity and are useful for treating warm blooded animals and mammals with rheumatoid arthritis, osteoarthritis, scleroderma, systemic lupus erythematosus, autoimmune deficiency syndrome, atopic dermatitis, cancer (particularly colon and melanoma), and psoriasis. Thus, this invention also relates to the pharmaceutical compositions containing lyxofuranoside compounds and methods of treating inflammatory and/or autoimmune disorders.

2. Description of the Related Art

The most reactive functional group in D-lyxose is the anomeric hydroxyl group. A glycoside is formed when the hydrogen atom of an anomeric hydroxyl group is replaced by a substituted or unsubstituted carbon atom. Typically, glycosides are formed either for group protection or as part of the synthesis of a larger molecule. The Fischer Method is particularly effective for synthesizing glycosides from unprotected reducing sugars and low molecular weight alcohols. After the glycosides are formed, various blocking methods are used to block or protect one or more of the hydroxyl group(s) thus leaving one or two hydroxyls free to derivatize. Isopropylidene and benzylidene groups are the most commonly used protective groups in carbohydrate chemistry. These groups are introduced into a molecule under similar conditions; however, the location of the protection can be quite different. The reason for this difference is directly related to the stability of each protected molecule. Since protection normally occurs under conditions which allow reversibility, reaction proceeds until equilibrium is reached. The distribution of products at equilibrium is determined by their relative thermodynamic stabilities. In other words, these reactions are thermodynamically controlled. Benzylidene groups prefer to be part of six-membered ring acetals, while the ketals resulting from acetonation generally are 5-membered rings. The difference is attributed to the effect of the methyl and phenyl substituents on the stability of the particular ring systems. These blocking methods are described in U.S. Pat. Nos. 2,715,121, 4,056,322, 4,735,934, 4,996,195, and 5,010,054 the disclosure of which are incorporated herein by reference. Other blocking methods are described in J. Carbohydr. Chem., 4, 227 (1985); 3, 331 (1984); Methods in Carbohydr. Chem., 1, 191 (1962); 1, 107 (1962); Can. J. Chem., 62, 2728 (1984); 47, 1195, 1455 (1969); 48, 1754 (1970). The therapeutic activity of hexoses and their derivatives are also disclosed in several of the above references.

A well known derivative of α-D glucose having beneficial therapeutic properties is Amiprilose. HCl, 1,2-0-isopropylidene-3-0-3'-(N',N'-dimethylaminopropyl)-α-D-glucofuranose. This compound, which is in late Phase III clinical trials, is known to have anti-inflammatory activity and demonstrated utility in managing the signs and symptoms of rheumatoid arthritis.

Unfortunately, while some of the prior art hexose derivatives have shown beneficial therapeutic activity, high doses of these compounds, including Amiprilose. HCl, are often needed to be effective and produce the desired results. Therefore, the prior art derivatives are difficult to prescribe orally. Because, therapy for inflammatory and autoimmune disorders is often midterm and long-term, there is a need to develop potent, non-toxic compounds which can be orally administered to promote ease of treatment and patient compliance.

One object of the present invention, therefore, is to provide a new class of compounds (pentofuranoside derivatives) that exhibit significantly greater potency than available compounds in order to provide ease of treatment, particularly oral administration. It is believed that the compounds of the present invention act by a different mechanism than Amiprilose. HCl and are more selective in their activity.

Another object of the present invention is to provide novel carbohydrate compounds (pentoses) that exhibit significantly greater potency for cancer treatment (particularly melanoma and colon cancer). There is no example available in the literature wherein pentoses, particularly lyxofuranoside derivatives, are used for treating cancer patients (particularly for treating melanoma and colon cancer patients).

Another object of the present invention is to provide a novel class of disubstituted or deoxy disubstituted lyxofuranoside compounds which exhibit anti-inflammatory and anti-proliferative activity. It is also an object of the present invention to provide novel compounds and compositions which are useful in the treatment of warm blooded animals and mammals having anti-inflammatory and/or autoimmune disorders. It is a further object of this invention to provide a novel, simple, and efficient process for preparing alkyl, aryl, aralkyl, or heterocyclic alkyl 2,3-0-(1-methlethylidene)-α-D-lyxofuranoside compounds.

A still further object of this invention to provide novel compounds that exhibit significantly increased potency over available compounds, such as Therafectin (Amiprilose. HCl), in order to provide ease of oral administration.

SUMMARY OF THE INVENTION

In order to achieve the above-mentioned objects and in accordance with the purpose of the invention as embodied and broadly described herein, there is provided a α-D-lyxofuranoside having the following general formula I:

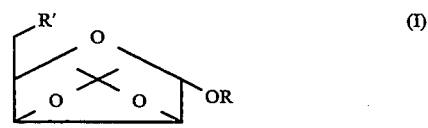

wherein

R is H, $C_5-C_{15}$-alkyl, n-$C_5-C_{15}$-alkyloxy-$C_2-C_4$-alkyl (preferably n-nonyloxypropyl and n-decyloxypropyl), and phenylpropyl;

$R^1$ is —$YR^2$, pyrrolidinyl, piperidinyl, morpholinyl, $C_5-C_{15}$-alkylamino, hexamethyleneimino, amino-$C_2C_4$-pyrrolidinyl (preferably $C_2$), amino-$C_2-C_5$-pyrrolidinyl (preferably n-$C_3$), amino-$C_2-C_4$-morpholinyl (preferably $C_2$), or amino-$C_2-C_4$-piperidinyl (preferably $C_2$);

wherein Y is O or S and $R^2$ is $C_5-C_{15}$-alkyl, N-$C_2-C_4$-pyrrolidinyl (preferably N-ethyl) N-$C_2-C_4$-piperidinyl (preferably N-ethyl), N-$C_2-C_4$-morpholinyl (preferably N-ethyl), N,N-dimethylaminopropyl, or hexamethyleneiminoethyl;

where nonyloxypropyl is—$(CH_2)_3$-O-$(CH_2)_8CH_3$ where N-$C_2$-$C_4$ piperidinyl is

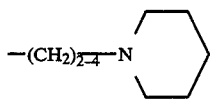

where pyrrolidinyl is

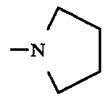

where aminoethylpyrrolidinyl is

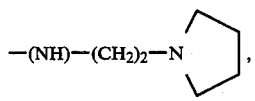

etc.

The present invention also provides pharmaceutical compositions for the treatment of inflammatory and/or autoimmune disorders. These compositions comprise an effective amount of at least one of the above-described lyxofuranoside compounds, or a physiological acceptable acid-addition salt thereof, with at least one pharmaceutically acceptable carrier. The lyxofuranoside compounds (pentose derivatives) of the present invention exhibit greater potency in terms of their activity (Con-A, Fibroblast, and Mixed Lymphocyte Response) than known glucofuranose compound (hexose derivative), such as THERAFECTIN (Amiprilose. HCl). These novel compounds have demonstrated in vitro decreased skin cell proliferation and the inhibition of the proliferative response of splenic T-lymphocytes to known mitogen. Since T-lymphocytes are the immune cells that regulate immune responses of the compounds of the present invention can be used for treating warm blooded animals and mammals with inflammatory and-/or autoimmune disorders such as rheumatoid arthritis, osteoarthritis, psoriasis, atopic dermatitis, scleroderma, systemic lupus erythematosus, and autoimmune deficiency syndrome. These compounds have also demonstrated a significant anti-cancer activity (particularly against melanoma and colon cancer) in in vitro screens. Also the compounds of the present invention can be administered internally or externally.

As mentioned above, the present invention is also directed to the novel synthesis of alkyl, alkoxyalkyl, aralkyl, or heterocyclic alkyl 2,3-0-(1-methlethylidene)-α-D-lyxofuranosides which are obtained in very good yield by periodate oxidation followed by reduction of the corresponding α-D-mannofuranoside.

DETAILED DESCRIPTION OF THE INVENTION

The compounds of the present invention are prepared by the following reaction sequences:

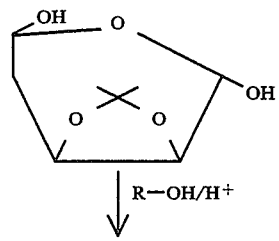

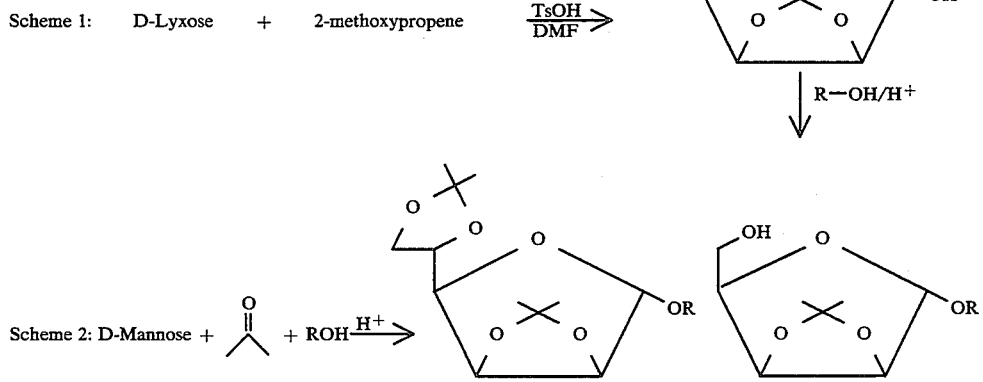

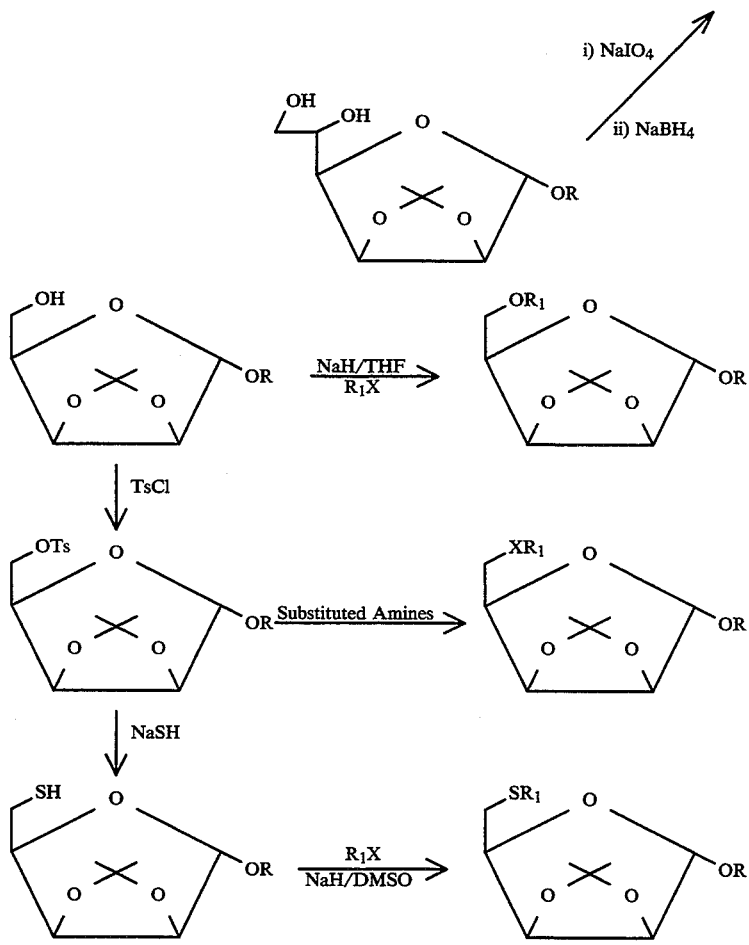

In scheme 1, D-lyxose is first treated with 2-methoxypropene to block 2,3-positions leaving behind only two hydroxyl groups, one at the anomeric position and the other at 5-position which are free to derivatize. The anomeric hydroxyl group, being more reactive, is then treated with a suitable alcohol in the presence of an acid catalyst form a glycoside. Alternatively, in scheme 2, D-mannose is treated with an aldehyde or ketone to block the 2,3 and 5,6-positions leaving only one hydroxyl group at the anomeric position free to derivatize. The anomeric hydroxyl group is then treated with an appropriate alcohol in the presence of acid catalyst to form a glycoside. The 5,6-blocked substituent could then be removed selectively, oxidized with periodate, and reduced to obtain the corresponding lyxofuranoside in good yields. These compounds are then treated with the desired side chains or are derivatized further. These compounds represent a novel class of compounds and there is no example available thus far wherein glycosides of disubstituted or deoxy disubstituted lyxofuranoses (pentoses) are used as a therapy for inflammatory or autoimmune disorders.

The compounds produced by these reactions are:

I. n-Dodecyl 2,3-0-(1-methlethylidene)-α-D-lyxofuranoside
II. n-Nonyloxypropyl 2,3-0-(1-methlethylidene)-α-D-lyxofuranoside
III. n-Nonyloxypropyl 2,3-0-(1-methlethylidene)-5-0-decyl-α-D-lyxofuranoside
IV. n-Nonyloxypropyl 2,3-0-(1-methlethylidene)-5-0-(N',N'-dimethylamino-n-propyl)-α-D-lyxofuranoside
V. n-Nonyloxypropyl 2,3-0-(1-methlethylidene)-5-0-N'-ethylpyrrolidinyl-α-D-lyxofuranoside
VI. n-Nonyloxypropyl 2,3-0-(1-methlethylidene)-5-0-N'-ethylpiperidinyl-α-D-lyxofuranoside
VII. n-Nonyloxypropyl 2,3-0-(1-methlethylidene)-5-0-N'-ethylmorpholinyl-α-D-lyxofuranoside
VIII. n-Nonyloxypropyl 2,3-0-(1-methylethylidene)-5-0-hexamethyleneiminoethyl-α-D-lyxofuranoside
IX. Phenylpropyl 2,3-0-(1-methylethylidene)-5-0-decyl-α-D-lyxofuranoside
X. Phenylpropyl 2,3-0-(1-methylethylidene)-5-0-(N',N'-dimethylamino-n-propyl-α-D-lyxofuranoside
XI. Phenylpropyl 2,3-0-(1-methylethylidene)-5-0-N-ethylpyrrolidinyl-α-D-lyxofuranoside
XII. Phenylpropyl 2,3-0-(1-methylethylidene)-5-0-N'-ethylpiperidinyl-α-D-lyxofuranoside
XIII. n-Phenylpropyl 2,3-0-(1-methylethylidene)-5-0-N'-ethylmorpholinyl-α-D-lyxofuranoside
XIV. Phenylpropyl 2,3-0-(1-methylethylidene)-5-0-hexamethyleneiminoethyl-α-D-lyxofuranoside
XV. n-Dodecyl 5-deoxy-2,3-0-(1-methylethylidene)-5-aminoethylpyrrolidinyl-α-D-lyxofuranoside
XVI. n-Nonyloxypropyl 5-deoxy-2,3-0-(1-methylethylidene)-5-pyrrolidinyl-α-D-lyxofuranoside
XVII. n-Nonyloxypropyl-5-deoxy-2,3-0-(1-methylethylidene)-5-piperidinyl-α-D-lyxofuranoside
XVIII. n-Nonyloxypropyl-5-deoxy-2,3-0-(1-methylethylidene)-5-morphilinyl-α-D-lyxofuranoside XIX. n-Nonyloxypropyl 5-deoxy 2,3-0-(1-methylethylidene)-5-aminoheptyl-α-D-lyxofuranoside XX. n-Nonyloxypropyl 5-deoxy-2,3-0-(1-methylethylidene)-5-aminoethylpiperidinyl-α-D-lyxofuranoside XXI. n-Nonyloxypropyl 5-deoxy-2,3-0-(1-methylethylidene)-5-aminoethylmorpholinyl-α-D-lyxofuranoside XXII. n-Nonyloxypropyl 5-deoxy-2,3-0-(1-methylethylidene)-5-hexamethyleneiminoethyl-α-D-lyxofuranoside XXIII. n-Nonyloxypropyl 5-deoxy-2,3-0-(1-methylethylidene)-5-aminoethylpyrrolidinyl-α-D-lyxofuranoside XXIV. n-Nonyloxypropyl 5-deoxy-2,3-0-(1-methylethylidene)-5-aminopropylpyrrolidinyl-α-D-lyxofuranoside XXV. Phenylpropyl 5-deoxy-2,3-0-(1-methylethylidene)-5-pyrrolidinyl-α-D-lyxofuranoside XXVI. Phenylpropyl 5-deoxy-2,3-0-(1-methylethylidene)-5-piperidinyl-α-D-lyxofuranoside XXVII. Phenylpropyl 5-deoxy-2,3-0-(1-methylethylidene)-5-morpholinyl-α-D-lyxofuranoside XXVIII. Phenylpropyl 5-deoxy-2,3-0-(1-methylethylidene)-5-hexamethyleneimino-α-D-lyxofuranoside XXIX. Phenylpropyl 5-deoxy-2,3-0-(1-methylethylidene)-5-aminononyl-α-D-lyxofuranoside XXX. Phenylpropyl 5-deoxy-2,3-0-(1-methylethylidene)-5-aminoethylpyrrolidene-U-D-lyxofuranoside XXXI. Phenylpropyl 5-deoxy-2,3-0-(1-methylethylidene)-5-aminopropylpyrrolidinyl-α-D-lyxofuranoside XXXII. Phenylpropyl 5-deoxy-2,3-0-(1-methylethylidene)-5-aminoethylpiperidinyl-α-D-lyxofuranoside XXXIII. Phenylpropyl 5-deoxy-2,3-0-(1-methylethylidene)-5-aminoethylmorpholinyl-α-D-lyxofuranoside XXXIV. n-Nonyloxypropyl 2,3-0-(1-methylethylidene)-5-S-n-decylα-D-lyxofuranoside XXXV. n-Nonyloxypropyl 2,3-0-(1-methylethylidene)-5-S-ethylpyrrolidinyl-α-D-lyxofuranoside XXXVI. n-Nonyloxypropyl 2,3-0-(1-methylethylidene)-5-S-ethylmorpholinyl-α-D-lyxofuranoside XXXVII. n-Nonyloxypropyl 2,3-0-(1-methylethylidene)-5-S-ethylpiperidinyl-α-D-lyxofuranoside A simple and efficient process for the synthesis of alkyl or substituted alkyl, aralkyl, or heterocyclic alkyl 2,3-(1-methylethylidene)-α-D-lyxofuranoside compounds is described above, which starts by reacting D-mannose with acetone and a suitable alcohol in the presence of a catalytic amount of concentrated sulfuric acid. The product obtained is hydrolysed selectively at 5,6-position followed by periodate oxidation and then reduced with sodium borohydride.

The disubstituted and deoxy disubstituted glycosides of lyxofuranoside derivatives of the present invention exhibit various pharmacological properties and are, therefore, useful for treating animals and mammals with inflammatory and or autoimmune disorders. Several intermediates described herein may be prepared by methods described in my copending U.S. application, Ser. No. 07/923,452.

The free amino compounds described above are basic and form organic and inorganic acid salts which are useful in the therapeutic composition and method of invention. These may be prepared by the usual prior art techniques, such as suspending the compound in water and then adding exactly one equivalent of the desired organic acid or mineral acid. Examples of suitable acids include HCl, $H_2SO_4$, $HNO_3$, maleic acid, benzoic acid, tartaric acid, acetic acid, p-aminobenzoic acid, oxalic acid, succinic acid, and glucuronic acid. The neutral solution of the resulting salt is subjected to rotary evaporation under diminished pressure to the volume necessary to assure precipitation of the salt upon cooling, which is then filtered and dried. The salts of the present invention may also be prepared strictly under non-aqueous conditions, for example, dissolving the free amine in ether and adding exactly one equivalent of the desired acid in ether. Stirrina the solution at 0°–5° C. causes the precipitation of the amine salt which are filtered, washed with ether and dried. The amine salts are often preferred for use in formulating the therapeutic compositions of the invention as they are crystalline and relatively more stable and non-hygroscopic. The amine salts are also better adapted for intramuscular injection than are the free amines.

Because of their valuable pharmacological properties, the compounds of the present invention may be administered to human patients or to animals either orally, topically, rectally, internasally or by parenteral administration. When the therapeutic composition is to be administered orally, the compounds of the present invention may be admixed with a prior art filler and or binder such as starch, and, if desired, a disintegrator, and the admixture pressed into a tablet of a size convenient for oral administration. Capsules also may be filled with the powdered therapeutic composition and administered orally. Alternatively, a water solution of the amine salt or suspension of the therapeutic composition may be admixed with a flavored syrup and administered orally. A salt of the free amine is usually preferred where the compound is administered by intramuscular injection.

The present pharmaceutical compositions are preferably produced and administered in dosage units, each unit containing as active component a certain amount of at least one compound of the present invention and or at least one of its physiologically acceptable acid addition salts. The dosage may be varied over extremely wide limits as the compounds are effective at low dosage levels are relatively free of toxicity. The compounds may be administered in the minimum quantity which is therapeutically effective, and the dosage may be increased as desired up to the maximum dosage tolerated by the patient. In the case of an animal or human, the effective dose to treat autoimmune and or anti-inflammatory disorders can range from 1 to 50 mg per kilogram of body weight per day, preferably an amount of about 2–30 mg per kilogram per day, over a period required for the treatment. In the case of in vitro testing, the effective amount necessary to achieve 50% inhibition of the cultured cells ranges from 1–100 μg per ml of the cultured medium, preferably 2–50 μg per ml.

The following examples demonstrate the synthesis of several compounds according to this invention and illustrate the beneficial therapeutic properties of these compounds. The examples described are illustrative, and are not to be considered as limitative in any manner of the claims which follow.

EXPERIMENTAL PROCEDURE

Various solvents, such as acetone, methanol, pyridine, tetrahydrofuran, dimethylsulfoxide, ether, hexanes, and ethylacetate were dried using various drying reagents by the procedure as described in the literature. Wet solvents gave poor yields of the products or intermediates. IR spectra were recorded as nujol mulls or a thin neat film on a Beckman Instrument using sodium chloride plates. PMR, CMR, and various 2D spectra were recorded on a Varian XL-300 MHz instrument using tetramethylsilane as an internal standard reference. CIMS were obtained on a Finnigan MAT-4510 mass spectrometer equipped with an INCOS data system. Generally, a direct exposure probe was used and methane was used as a reagent gas (0.35 mm Hg, 120° C. source temperature).

EXAMPLE 1

Preparation of Phenylpropyl 2,3-0-(1-methylethylidene)-α-D-lyxofuranoside

Scheme 1:

Phenylpropyl 2,3-0-(1-methylethylidene)-α-D-mannofuranoside (prepared as described in U.S. application Ser. No. 07/923,452 (20.0 gms) was suspended in water (40 ml) and the flask cooled to 0°–5° C. Sodium periodate (20 gms) was dissolved in water (40 ml) by warming and added to the above solution slowly (5 min). The reaction mixture was stirred at the same temperature for 30 minutes and then 200 ml of ethanol was added to precipitate out all the salts. Filtered off the salts and washed with 50 ml more of ethanol. The solvents were removed from the liltrate and the residue dissolved in ether (200 ml), dried over MgS$_4$, filtered, and solvent removed.

The crude aldehyde so formed was dissolved in methanol (200 ml) and added sodium borohydride (7 gm) in portions, at 5°–10° C. The reaction mixture was stirred at the same temperature for 90 minutes. The excess sodium borohydride was then decomposed by the addition of acetone (10 ml) and the resulting solution subjected to rotary evaporation to remove all the solvents. The residue was dissolved in ethylacetate (200 ml) and washed with brine (30 ml). The organic layer was dried over magnesium sulfate, filtered, and solvent removed. The product so obtained showed a single homogenous spot on a TLC plate and could be used in further steps without any further purification. The yield of the pure viscous oil was 15 g (82.3%).

CIMS: 309 (M+1).

Scheme 2:

To a solution of D-lyxose (30 g) in dry DMF (150 ml) at 0° C. was added 2-methoxypropene (40 ml, 2 eq.) and a catalytic amount of p-toluenesulfonic acid (1 g). After stirring at 0°–5° C. for 3 hours, the reaction mixture was neutralized with triethylamine. The solvents were then stripped off and the residue was purified by column chromatography using 50% ethylacetate in hexane. The yield of the pure product, 2,3-0-(1-methylethylidene)-α-D-lyxofuranose was 52%, m.p. 82°–83° C. (literature m.p. 80°–82° C., Carbohydrate Research, 219,115(1991).

The lyxofuranose (5 gm) obtained above was dissolved in dioxane (30 ml) and added 3-phenyl-l-propanol (5 ml) and a catalytic amount of concentrated sulfuric acid (5 drops). The reaction mixture was refluxed for one hour and then cooled to ambient temperature. Neutralized the reaction with triethylamine and stripped off the solvents. The residue was dissolved in ethylacetate (100 ml), washed with water (1×10 ml), the organic layer dried (MgSO$_4$, filtered and solvent removed. The product, phenylpropyl 2,3-0-(1-methylethylidene)-α-D-lyxofuranoside, was purified by flash chromatography. The yield of the pure product was 84%.

CIMS: 309 (M+1).

Other compounds which were prepared similarly as described in Example 1 (Schemes 1 and 2) are:
  i. n-Nonyloxypropyl 2,3-0-(1-methylethylidene)-α-D-lyxofuranoside.
  ii. n-Dodecyl 2,3-0-(1-methylethylidene)-α-D-lyxofuranoside.

EXAMPLE 2

Preparation of phenylpropyl 2,3-0-(1-methylethylidene)-5-0-n-decyl-α-D-lyxofuranoside.

Sodium hydride (60%, 0.4 g) was made free of oil by washing with hexane and added dry DMSO (20 ml). To this stirred solution was added a solution of phenylpropyl 2,3-0-(1-methylethylidene)-α-D-lyxofuranoside (3.08 g; 0.01 mol) in DMSO (10 ml), dropwise, over a period of 10 minutes at room temperature. The reaction was stirred at the same temperature for 30 minutes. 1-Bromodecane (2.65 g; 0,012 mol) was then added dropwise over a period of ten minutes and the mixture stirred for another 3 hours. The reaction mixture was poured into ice cold water (200 ml) and extracted with ether (3×50 ml). The combined ether extract was washed once with water (20 ml), ether layer dried (MgSO$_4$), filtered and solvent removed. The crude product so obtained was purified by flash chromatography using 5% ethylacetate in hexane. The yield of pure product (viscous oil) was 96%. CIMS: 449 (M+1)

Other compounds which were prepared as described in Example 2 are:
1. Phenylpropyl 2,3-0-(1-methylethylidene)-5-0-dodecyl-α-D-lyxofuranoside
2. Phenylpropyl 2,3-0-(1-methylethylidene)-5-0-(N',N'-dimethylamino-n-propyl)-α-D-lyxofuranoside
3. Phenylpropyl 2,3-0-(1-methylethylidene)-5-0-N'-ethylpyrrolidinyl-α-D-lyxofuranoside
4. Phenylpropyl 2,3-0-(1-methylethylidene)-5-0-N'-ethylpiperidinyl-α-D-lyxofuranoside
5. n-Phenylpropyl 2,3-0-(1-methylethylidene)-5-0-N'-ethylmorpholinyl-α-D-lyxofuranoside
6. Phenylpropyl 2,3-0-(1-methylethylidene)-5-0-hexamethyleneiminoethyl-α-D-lyxofuranoside

EXAMPLE 3

Preparation of n-Nonyloxypropyl 2,3-0-(1-methylethylidene)-5-0-decyl-α-D-lyxofuranoside Sodium hydride (60%, 0.4 g) was made free of oil by washing with hexane and added dry DMSO (20 ml). To this stirred solution was added a solution of n-nonyloxypropyl 2,3-0-(1-methylethylidene)-α-D-lyxofuranoside (3.74 g; 0.01 mol) in DMSO (10 ml), dropwise, over a period of 10 minutes at room temperature. The reaction was stirred at the same temperature for 30 minutes. 1-Bromodecane (2.65 g; 0,012 mol) was then added dropwise over a period of ten minutes and the mixture stirred for another 3 hours. The reaction mixture was poured into ice cold water (200 ml) and extracted with ether (3×50 ml). The combined ether extract was washed once with water (20 ml), ether layer dried (MgSO4), filtered and solvent removed. The crude product so obtained was purified by flash chromatography using 5% ethylacetate in hexane. The yield of the pure viscous oil was 92%.

CIMS: 515 (M+1)

Other compounds which were prepared similarly as described in Example 3 are as follows:
1. n-Nonyloxypropyl 2,3-0-(1-methylethylidene)-5-0-dodecyl-α-D-lyxofuranoside
2. n-Nonyloxypropyl 2,3-0-(1-methylethylidene)-5-0-(N',N'-dimethylamino-n-propyl)-α-D-lyxofuranoside
3. n-Nonyloxypropyl 2,3-0-(1-methylethylidene)-5-0-N-ethylpyrrolidinyl-α-D-lyxofuranoside
4. n-Nonyloxypropyl 2,3-0-(1-methylethylidene)-5-0-N'-ethylpiperidinyl-α-D-lyxofuranoside
5. n-Nonyloxypropyl 2,3-0-(1-methylethylidene)-5-0-N'-ethylmorpholinyl-α-D-lyxofuranoside
6. n-Nonyloxypropyl 2,3-0-(1-methylethylidene)-5-0-hexamethyleneiminoethyl-α-D-lyxofuranoside

EXAMPLE 4

Preparation of Phenylpropyl 2,3-0-(1-methylethylidene)-5-p-toluenesulfonyl-α-D-lyxofuranoside To a stirred solution of phenylpropyl 2,3-0-1-methylethylidene)-α-D-lyxofuranoside (33.8 g; 0.1 mol) in dry pyridine (100 ml) was added dropwise a solution of p-toluenesulfonyl chloride (22.8 g; 0.12 mol) in dry pyridine (150 ml), over a period of 20 minutes, at 0°–10° C. The progress of the reaction was monitored by tlc. After 5 hours the pyridine was removed under diminished pressure and the residue extracted with ethylacetate (400 ml), washed with a saturated solution of sodium bicarbonate (2×50 ml), brine (2×50 ml), and water (100 ml) . The organic layer was dried over MSO4, filtered and solvent removed. The residue on cooling and scratching with a small amount of hexane afforded a white crystalline material in 92% yield. It was recrystallized from ether-hexane of m.p 72–73 ° C.

CIMS: 463 (M+1).

The following tosylates were also prepared similarly as described in Example 4:
1. n-Dodecyl 2,3-0-(1-methylethylidene)-5-p-toluenesulfonyl-α-Dlyxofuranoside
2. n-Nonyloxypropyl 2,3-0-(1-methylethylidene)-5-p-toluenesulfonyl-α-D-lyxofuranoside

EXAMPLE 5

Preparation of Phenylpropyl 5-deoxy-2,3-0-(1-methylethylidene)-5-pyrrolidinyl-α-D-lyxofuranoside To a stirred solution of phenylpropyl 2,3-0-(1-methylethylidene)-5-0-p-toluenesulfonyl-α-D-lyxofuranoside (5 g) in anhydrous DMF was added pyrrolidine (5 ml) and the mixture heated at 80°–90° C. for 4 hours. DMF was then removed under diminished pressure and the residue dissolved in ethylacetate (100 ml), washed with NaHCO3 solution (1×10 ml) and brine (1×10 ml). The ethylacetate layer was dried over MgSO4, filtered and solvent removed. The residue so obtained was purified by column chromatography using 30% ethylacetate in hexane. The yield of the pure product was 89%

The following compounds were prepared similarly as explained in Example 5 by reacting phenylpropyl 2,3-0-(1-methylethylidene)-5-0-p-toluenesulfonyl-α-D-lyxofuranoside with a suitable primary or secondary amines:
1. Phenylpropyl 5-deoxy-2,3-0-(1-methylethylidene)-5-morpholinyl-α-D-lyxofuranoside
2. Phenylpropyl 5-deoxy-2,3-0-(1-methylethylidene)-5-hexamethyleneimino-α-D-lyxofuranoside
3. Phenylpropyl 5-deoxy-2,3-0-(1-methylethylidene)-5-aminoheptyl-α-D-lyxofuranoside
4. Phenylpropyl 5-deoxy-2,3-0-(1-methylethylidene)-5-aminoethylpyrrolidinyl-α-D-lyxofuranoside
5. n-Phenylpropyl 5-deoxy-2,3-0-(1-methylethylidene)-5-aminopropylpyrrolidinyl-α-D-lyxofuranoside
6. Phenylpropyl 5-deoxy-2,3-0-(1-methylethylidene)-5-aminoethylpiperidinyl-α-D-lyxofuranoside
Phenylpropyl 5-deoxy-2,3-0-(1-methylethylidene)-5-aminoethylmorpholinyl-α-D-lyxofuranoside

EXAMPLE 6

Preparation of n-nonyloxypropyl 5-deoxy-2,3-0-(1-methylethylidene)-5-pyrrolidinyl-α-D-lyxofuranoside To a stirred solution of n-nonyloxypropyl 2,3-0-(1-methylethylidene)-5-0-p-toluenesulfonyl-α-D-lyxofuranoside (5 g) in anhydrous DMF was added pyrrolidine (5 ml) and the mixture heated at 80°–90° C. for 4 hours. DMF was then removed under diminished pressure and the residue dissolved in ethylacetate (100 ml), washed with NaHCO3 solution (1×10 ml) and brine (1×10 ml). The ethylacetate layer was dried over MgSO4, filtered and solvent removed. The residue so obtained was purified by column chromatography using 30% ethylacetate in hexane. The yield of the pure product was 94%.

CIMS: 428 (M+1)

The following compounds were prepared similarly as explained in Example 5 by reacting n-nonyloxypropyl 2,3-0-(1-methylethylidene)-5-0-p-toluenesulfonyl-α-D-lyxofuranoside with a suitable primary or secondary amines:
1. n-Nonoyloxypropyl 5-deoxy-2,3-0-(1-methylethylidene)-5-pyrrolidinyl-α-D-lyxofuranoside
2. n-Nonoyloxypropyl 5-deoxy-2,3-0-(1-methylethylidene)-5-piperidinyl-α-D-lyxofuranoside
3. n-Nonyloxypropyl 5-deoxy-2,3-0-(1-methylethylidene)-5-morphilinyl-α-D-lyxofuranoside
4. n-Nonyloxypropyl 5-deoxy 2,3-0-(1-methylethylidene)-5-aminoheptyl-α-D-lyxofuranoside
5. n-Nonyloxypropyl 5-deoxy-2,3-0-(1-methylethylidene)-5-aminoethylpiperidinyl-α-D-lyxofuranoside
6. n-Nonyloxypropyl 5-deoxy-2,3-0-(1-methylethylidene)-5-aminoethylmorpholinyl-α-D-lyxofuranoside
7. n-Nonyloxypropyl 5-deoxy-2,3-0-(1-methylethylidene)-5-hexamethyleneiminoethyl-α-D-lyxofuranoside
8. n-Nonyloxypropyl 5-deoxy-2,3-0-(1-methylethylidene)-5-aminoethylpyrrolidinyl-α-D-lyxofuranoside
9. n-Nonyloxypropyl 5-deoxy-2,3-0-(1-methylethylidene)-5-aminopropylpyrrolidinyl-α-D-lyxofuranoside

EXAMPLE 7

Preparation of n-Dodecyl 5-deoxy-2,3-0-(1-methylethylidene)-5-ethylpyrrolidinyl-α-D-lyxofuranoside To a stirred solution of n-dodecyl 2,3-0-(1-methylethlidene)-5-0-ptoluenesulfonyl-α-D-lyxofuranoside (5 g) in anhydrous DMF was added 1-(2-aminoethyl) pyrrolidine 5 ml and mixture heated at 80°-90° C. for 4 hours. DMF was then removed under diminished pressure and the residue dissolved in ethylacetate (100 ml), washed with NaHCO$_3$ solution (1×10 ml) and brine (1×10 ml). The ethylacetate layer was dried over MgSO$_4$, filtered and solvent removed. The residue so obtained was purified by column chromatography using 30% ethylacetate in hexane. The yield of the pure product was 88%.

CIMS: 455 (M+1)

EXAMPLE 8

Preparation of n-nonyloxypropyl 5-deoxy-2,3-0-(1-methylethylidene)-5-S-2'-ethylpyrrolidinyl-α-D-lyxofuranoside Step 1 n-Nonyloxypropyl 5-deoxy-2,3-0-(1-methylethlidene)-5-thio-α-Dlyxofuranoside To a stirred solution of n-nonyloxypropyl 2,3-0-(1-methylethylidene)-5-p-toluenesulfonyl-α-D-lyxofuranoside (as obtained in example 4) (10 g) in methanol (150 ml) was added NaSH.XH$_2$O (10 g) and the mixture refluxed for 3 hours. Solvent was then removed using rotary evaporator and the residue extracted with ethyl acetate (150 ml), washed well with water (3×50 ml), sodium bicarbonate solution (2×50 ml), the organic layer dried (MgSO$_4$), filtered, and solvent removed. The residue so obtained was purified using flash chromatography and eluting with 5% ethyl acetate in hexane. The yield of the pure product was 78%.

CIMS: 391 (M+1).

Step 2 n-Nonyloxypropyl 5-deoxy-2,3-0-(1-methylethylidene)-5-S-2'ethylpyrrolidinvl-α-D-lyxofuranoside Sodium hydride (60%, 0.4 g) was made free of oil by washing with hexane and added dry DMSO (20 ml). To this stirred solution was added a solution of n-nonyloxypropyl 5-deoxy-2,3-0-(1-methylethylidene)-5-thio-α-D-lyxofuranoside (3.90 g; 0.01 mol) in DMSO (10 ml), dropwise, over a period of 10 minutes at room temperature. The reaction was stirred at -the same temperature for 30 minutes. 1-(2-chloroethyl)pyrrolidine (1.59 g; 0.012 mol) was then added dropwise over a period of ten minutes and the mixture stirred for another 3 hours. The reaction mixture was poured into ice cold water (200 ml) and extracted with ether (3×50 ml). The combined ether extract was washed once with water (20 ml), ether layer dried (MgSO$_4$), filtered and solvent removed. The crude product so obtained was purified by flash chromatography using 15% ethylacetate in hexane. The yield of the pure viscous oil was 81%.

CIMS: 488 (M+1)

Other compounds which were prepared similarly are:
1. n-Nonyloxypropyl 5-deoxy-2,3-0-(1-methylethylidene)-5-S-n-decyl-α-D-lyxofuranoside
2. n-Nonyloxypropyl 5-deoxy-2,3-0-(1-methylethylidene)-5-S-ethylmorpholinyl-α-D-lyxofuranoside
3. n-Nonyloxypropyl 5-deoxy-2,3-0-(1-methylethylidene)-5-S-ethylpiperidinyl-α-D-lyxofuranoside

PHARMACOLOGICAL ACTIVITY

The compounds of the present invention have demonstrated immunomodulatory and anti-inflammatory effects in biological assays. Various standard in vitro assays have been performed on most of the compounds of the present invention to ascertain immunomodulatory and anti-proliferative activities. These include:
i Mixed lymphocyte response (MLR).
ii BUD-8 human cell line fibroblast proliferation assay.
iii Concanavalin A assay (the mouse spleen cell mitogen induced blastogenesis).

The MLR assay measures the effects of a study compound on the activation and antigen presentation of T-lymphocytes, therefore determining immunomodulatory properties. The mouse spleen cell mitogen-induced blastogenesis and the BUD-8 human fibroblast proliferation assays measure the effects of the compounds of the present invention on cellular proliferation of cells involved in the pathogenesis of autoimmune diseases. These two assays are appropriate as screens to ascertain anti-inflammatory and/or autoimmune diseases.

The MLR is a classical assay used to measure T cell function by studying the proliferation response of T cells which are activated in vitro by genetically disparate stimulator cells. This is accomplished by co-culturing spleen cells from two different strains of mice. Splenic T cell proliferation occurs as a result of cellular activation signals generated by the ongoing cellular interactions.

In performing MLR assays, BALB/CBYJ mice were euthanized by cervical dislocation and their spleens removed. Single cell suspensions were prepared in culture medium (RPMI-1640 with hepes supplemented with 10% calf serum, 2 mM glutamine, 500 units penicillin/streptomycin and $4 \times 10^{-5}$ M 2-mercaptoethanol) using a Teflon pestle. The cells were centrifuged at 1500 RPM and the pellets resuspended in ACT (0.15 M Tris, 0.14 M ammonium chloride, pH 7.2 ) in order to lyse the red blood cells. After a 5 minutes incubation at 37° C. waterbath, the cells were washed and resuspended in culture medium. The splenic lymphocytes were counted. C57BL/6J spleen cells, which were used as stimulator cells, were prepared in the same way. The stimulator cells were treated with 50 μm/ml of mitomycin C for 20 minutes at 37° C., then washed five times in culture medium. The proliferative response were measured by culturing $5 \times 10^5$ responder spleen cells with $5 \times 10^5$ stimulator cells in 96-well microtiter plates in the presence or absence of test article or vehicle (DMSO). Syngeneic control cultures using mitomycin C treated normal BALB/C spleen cells as the stimulator cells were also run. All cultures were run in triplicate.

Solutions of compounds of the present invention in DMSO were prepared at a stock concentration of 300 mM. Solutions were made in a culture medium to a concentration of 1, 10, 30, 100, and 300 μM. The vehicle DMSO was used as a negative control.

After incubation for 5 days at 37° C. with 5% carbon dioxide, the amount of cell proliferation was measured by adding 20 μl of MTT (10 mg/ml in PBS) (3-[4,5-dimethylthiazol-2-yl]-2,5-diphenyltetrazolium bromide) to each well. plates were incubated for 4 hours at 37° C., after which 180 μl of supernatant was removed and 180 μl of 10% SDS in PBS was added. After an overnight incubation, the optical density (OD) of each well was read on a Molecular Devices microplate reader at 570-650 nm.

The results were determined by calculating the difference between the means of the allogeneic cultures and the means of the syngeneic cultures for each test compound concentration. Differences of the test article groups were compared to the difference of the control group. The percent change from the control was determined and an IC$_{50}$ estimated. The criteria used to establish activity levels were:

Estimated I$_{50}$

Inactive: >300 μM
Weak: >100 but<300 μM
Moderate: >30 but<100 μM
Strong: <30 μM

Sixteen (16) novel compounds were assayed for their ability to modulate a Mixed Lymphocyte Response in vitro. The test compounds were added to MLR cultures to give final concentrations of 1, 10, 30, 100, and 300 μm. The responses observed in the test article treated wells were compared to the control wells. DMSO did not appear to have any effect on the response. The results for the test compounds are shown in Table 1. Based on the estimated IC$_{50}$ all the test compounds were strong inhibitors of the MLR.

A second assay was conducted to demonstrate inhibitory activity of the compounds of the present invention to the in vitro proliferation of human skin cells in tissue culture. The skin cell fibroblast line, BUD-8, was originally derived from the normal skin of a 56 year old white female and can now be obtained from the American Type Culture Collection, Rockville, Md. The concentration of the compounds which were used in this assay were: 1, 10, 30, 100, and 300 μM. The vehicle was used as the negative control. Test compounds were prepared in DMSO at a stock concentration of 300 μM. Appropriate dilutions were made in culture medium.

In this assay BUD-8 cells were collected, counted, and diluted to 2×10$^4$ cells/ml. 0.1 ml was plated per well to give 2×10$^3$ cells/well. The compounds of the present invention were diluted in culture medium to the appropriate concentrations. Aliquotes of 100 μl were distributed to triplicate wells. Control wells with vehicle and wells with media were also run. After a three day incubation at 37° C. with 5% carbon dioxide, proliferation was measured by adding 20 μl of MTT (10 mg/ml in PBS) (3-[4,5-dimethyl thiazol-2-yl]-2,5diphenyl-tetrazolium bromide) to each well. Plates were incubated for 4 hours at 37° C., after which 180 μl of 10% SDS in PBS were added. After an overnight incubation, the optical density (OD) of each well was read using a Molecular Devices microplate reader at 570–650 nm.

Duplicate cultures were also set up to measure viability. After 3 days of incubation, supernatants were assayed for lactate dehydrogenase (LDH) activity to determine the viability of the cells, which is an indication of the toxicity of the test article on the BUD-8 cells. 0.1 ml of supernatent was mixed with 0.1 ml of the LDH substrate mixture which contains 5.4×10-2 M L(+) lactate, 6.6×10$^{-4}$ M 2-p-iodophenyl-3-p-nitrophenyl tetrazolium chloride, 2.8×10$^{-4}$ M phenazine methosulfate, 1.3×10$^{-3}$ M AND, and 0.2 M Tris buffer. PH 8.2. Plates were read immediately for 5 minutes at 490 nm using a Molecular Devices microplate reader.

The mean for each test article treated group was determined and compared to the mean of the control group. The percent change from the control was calculated, and the IC$_{50}$ estimated. The criteria used to establish activity levels were:

Estimated IC$_{50}$

Inactive: ≧300 μM
Weak: ≧100 but<300 μM
Moderate: ≧30 but<100 μM
Strong: <30 μM

Sixteen (16) test articles were assayed for their ability to inhibit fibroblast proliferation. The test article were added to BUD-8 cell cultures to give final concentrations of 1, 10, 30, 100, and 300 μM. The proliferation observed in the test article treated wells were compared to the DMSO control wells. The results of the test articles are shown in Table 1.

A third assay was conducted to demonstrate the ability of the compounds of the present invention to modulate T-lymphocyte activity. It is known that the induction and maintenance of most inflammatory diseases are typically due to the unrestricted activity of T-lymphocytes. Therefore, it is advantageous to identify compounds which are modulators of T-lymphocyte activity for eventual use in the regulation of inflammatory diseases, including acquired immune deficiency syndrome, psoriasis, systemic lupus, erythromatosus, and rheumatoid arthritis.

A simple method is used to screen compounds for their ability to modulate T-lymphocyte activity which comprises assessing the capacity of the compounds to alter the activation of murine spleen cells in response to T-lymphocyte mitogen activators, such as Conconavalin-A (Con-A). The method used to measure the effects of the compounds of the present invention on the blastogenic response of spleen cells to the T-lymphocyte mitogen (Con-A) is as follows:

The response of a mouse spleen cells to the T cell mitogen ConA is a classical assay. In this assay, mice were euthanized by cervical dislocation and their spleens removed surgically. A single cell suspension of the spleens was prepared in culture medium (RPMI-1640 with hepes, supplemented with 10% calf serum, 2 mM glutamine, 500 units penicillin/streptomycin, and 4×10$^{-5}$ M 2-mercaptoethanol) using a Teflon pestle. The cells were centrifuged at 1500 RPM and the pellets resuspended in ACT (0.15 M Tris, 0.14 M Ammonium chloride, pH 7.2) in order to lyse the red blood cells. After a five minutes incubation in 37° C. waterbath, the cells were washed and resuspended in culture medium. The splenic lymphocytes were counted using an electronic Coulter Counter and diluted to 5.0×10$^6$ cells/mi.

The test articles were diluted in culture medium to the appropriate concentrations. Aliquots 100 μl were distributed to triplicate wells in a 96-well microtiter plate. 50 μl of lymphocytes (2.5×10$^5$ cells) were added to each well. Control wells with vehicle and wells with media were also run. Plates were incubated for one hour at 37° C. 50 μl of Con-A (5 μl/ml) were then added to the wells to result in a final concentration of 1.25 μg/ml. After incubation at 37° C. with 5% carbon dioxide for 3 days, proliferation was measured by adding 20 μl of MTT (10 mg/mlin PBS) [3-(4,5-dimethyl-thiazol-2-yl)-2,5-diphenyltetrazoliumbromidel to each well. Plates were incubated for 4 hours at 37° C., after which 180 μl of 10% SDS in PBS were added. After an overnight incubation, the optical density (OD) of each well was read using a Molecular Devices microplate reader at 570–650 nm.

Duplicate cultures without Con-A were also set up. After 3 days of incubation, supernatants were assayed for lactate dehydrogenase activity to determine the viability of the cells, which is an indication of the toxicity of the test article on the splenic lymphocytes. 0.1 ml of supernatant was mixed with 0.1 ml of the LDH substrate mixture which contains $5.4 \times 10^{-2}$ M L(+) lactate, $6.6 \times 10^{-4}$ M 2-p-iodophenyl-3-p-nitrophenyl tetrazolium chloride, $2.8 \times 10^{-4}$ M phenazine methosulfate, $1.3 \times 10^{-3}$ M AND, and 0.2 M Tris buffer, pH 8.2. Plates were read immediately for 5 minutes at 490 nm using a Molecular Devices microplate reader.

The mean for each test article treated group was determined and compared to the mean of the control group. The percent change from the control was calculated, and the $IC_{50}$ was estimated.

The criteria used to establish activity levels were:

Estimated $IC_{50}$

Inactive: $\geq 300$ μM
Weak: $\geq 100$ but $< 300$ μM
Moderate: $\geq 30$ but $< 100$ μM
Strong: $< 30$ μM Sixteen (16) test articles were assayed for their ability to modulate a Con-A response in vitro. The test article were added to Con-A cultures to give a final concentrations of 1, 10, 30, 100, and 300 μM. The response observed in the test article treated wells were compared to the control wells. DMSO alone had little effect on the response. The results for the test articles are shown in Table 1.

The compounds of the present invention were also tested against various tumor cell lines, derived from seven cancer types. These include leukemia, melanoma, lung cancer, colon cancer, renal cancer, ovarian cancer, and brain cancer. Most of the compounds have shown significant activity in various screens, particularly against colon cancer and melanoma. The results of the test articles Average $GI_{50}$) are shown in Table 1.

The compounds of the present invention have demonstrated significant immunomodulatory and antiproliferative properties when tested in the aforementioned in vitro assays. The concentration tested ranged from 1 μM to 300 μM, with the most efficacious activities defined as one-half the maximal inhibitory concentrations ($IC_{50}$) or ($GI_{50}$) of 30 μM of less.

TABLE 1

| Compound # | MLR $IC_{50}$ (μm) | Con A $IC_{50}$ (μm) | Fibroblast $IC_{50}$ (μm) | GI (μM) |
|---|---|---|---|---|
| V. | <1 | 2.9 | 28 | −5.25 |
| VI. | 0.5 | 2.7 | >100 | NA |
| X. | <1 | 55 | 299 | −4.04 |
| XVI. | <1 | 3.5 | 58 | −5.29 |
| XXIV. | 0.85 | 2.5 | 16 | NA |
| XXV. | 12 | 25 | 200 | −4.02 |
| XXIX. | 1.5 | 5 | 20 | −4.49 |

While the present invention has been described in terms of its specific embodiments, certain modifications and equivalents will be apparent to those skilled in art and are intended to be included within the scope of the present invention, which is to be limited only by scope of the appended claims.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A pentofuranoside compound of formula I

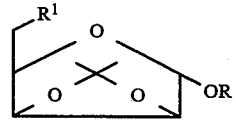

wherein R is nonyloxypropyl or phenylpropyl;
$R^1$ is -$YR^2$ or pyrrolidinyl, $C_5$-$C_{15}$ -alkylamino, or amino-$C_2$-$C_5$-pyrrolidinyl;
Y is O and
$R^2$ is N-$C_2$-$C_4$-pyrrolidinyl or N-$C_2$-$C_4$-piperidinyl.

2. A compound according to claim 1, selected from the group consisting of:
n-Nonyloxypropyl 2,3-0-(1-methylethylidene)-5-0-N-ethylpyrrolidinyl-α-D-lyxofuranoside,
n-Nonyloxypropyl 2,3-0-(1-methylethylidene)-5-0-N'-ethylpiperidinyl-α-D-lyxofuranoside,
n-Nonyloxypropyl 5-deoxy-2,3-0-(1-methylethylidene)-5-pyrrolidinyl-α-D-lyxofuranoside,
n-Nonyloxypropyl 5-deoxy-2,3-0-(1-methylethylidene)-5-aminopyrrolidinyl-α-D-lyxofuranoside and
Phenylpropyl 5-deoxy-2,3-0-(1-methylethylidene)-5-aminononyl-α-D-lyxofuranoside.

3. A compound according to claim 1 wherein $R^2$ is selected from the group consisting of N-ethylpyrrolidinyl, and N-ethylpiperidinyl.

4. A pharmaceutical composition for the treatment of inflammatory disorders which comprises a therapeutically effective amount of a compound according to claim 1, or a physiologically acceptable acid-addition salt thereof, and a pharmaceutically acceptable carrier.

5. A method of treating an animal suffering from inflammatory disorders which comprises administering thereto an effective amount of a compound of claim 1 or a physiologically acceptable acid-addition salt thereof.

6. The method of claim 5, wherein said compound is administered orally.

7. The method of claim 5, wherein said compound is administered parenterally.

8. The method of claim 5, wherein said animal is suffering from psoriasis.

9. A compound according to claim 1 wherein R is n-nonyloxypropyl.

10. A compound according to claim 1 wherein R is phenylpropyl.

11. The method of claim 5 wherein the animal is a human.

12. The method of claim 8 wherein the animal is a human.

* * * * *